(12) United States Patent
Malchesky et al.

(10) Patent No.: US 6,171,551 B1
(45) Date of Patent: Jan. 9, 2001

(54) ELECTROLYTIC SYNTHESIS OF PERACETIC ACID AND OTHER OXIDANTS

(75) Inventors: Paul S. Malchesky, Painesville Township; Chung-Chiun Liu, Cleveland Hts.; Tom L. Merk, Chesterland, all of OH (US)

(73) Assignee: Steris Corporation, Mentor, OH (US)

( * ) Notice: Under 35 U.S.C. 154(b), the term of this patent shall be extended for 0 days.

(21) Appl. No.: 09/130,814

(22) Filed: Aug. 7, 1998

Related U.S. Application Data

(60) Provisional application No. 60/073,905, filed on Feb. 6, 1998.

(51) Int. Cl.⁷ .................................................. A61L 9/00
(52) U.S. Cl. ........................... 422/29; 205/473; 205/687; 422/31; 422/32; 422/33; 422/292; 422/293
(58) Field of Search ................. 422/29, 31, 32, 422/33, 292, 293; 204/518, 194, 408, 409, 415, 232; 205/98–100, 473, 538, 626, 687

(56) References Cited

U.S. PATENT DOCUMENTS

| | | | |
|---|---|---|---|
| 4,101,394 | * 7/1978 | Johnson | 204/77 |
| 4,560,455 | 12/1985 | Porta et al. | 204/130 |
| 5,316,740 | 5/1994 | Baker et al. | 422/186.07 |
| 5,385,711 | 1/1995 | Baker et al. | 422/186.07 |
| 5,503,720 | 4/1996 | Teske | 205/787 |
| 5,705,050 | * 1/1998 | Sampson et al. | 205/687 |

FOREIGN PATENT DOCUMENTS

| | | |
|---|---|---|
| 0 115 893 | 8/1984 | (EP) . |
| 0 244 565 | 2/1987 | (EP) . |
| 0 658 763 | 6/1995 | (EP) . |
| 05302287 | 11/1993 | (JP) . |
| WO 93/18854 | 9/1993 | (WO) . |

OTHER PUBLICATIONS

N.E. Khomutov, et al. "The Kinetic Study of Anodal Processes in Potassium Acetate Solutions," *Izv. Vyssh. Uchebn. Zaved Khim. Technol.*, 31(11) pp. 71–74 (1988) (541.138) (Russian) (Translation of foreign document enclosed.)

Chernik, et al., "Ozone Evolution at the Lead Dioxide Electrode in Sulfuric and Perchloric Acid Solutions," Russian Journal of Electrochemistry, vol. 33, No. 3, pp. 264–267 (1997).

Shepelin, et al., "New Lead Dioxide Anode Design For Ozone Electrosynthesis," Plenum Publishing Corporation, pp. 1021–1027 (1991).

T. Takada, et al., "Aqueous ozone detector using $In_2O_3$ thin-film semiconductor gas sensor," Sensors and Actuators B 24–25, pp. 548–551 (1995).

* cited by examiner

*Primary Examiner*—Krisanne Thornton
(74) *Attorney, Agent, or Firm*—Fay, Sharpe, Fagan, Minnich & McKee, LLP

(57) ABSTRACT

An electrolysis unit (10) has an ion selective barrier (20) for separating an anodic chamber (12) from a cathodic chamber (14). An electrolyte within the unit includes a precursor, such as potassium acetate, or acetic acid. A positive potential is applied to an anode (16) within the anodic chamber, resulting in the generation of a variety of shorter and longer lived oxidizing species, such as peracetic acid, hydrogen peroxide, and ozone. In one preferred embodiment, a solution containing the oxidizing species is transported to a site where articles, such as medical instruments, are to be decontaminated. The oxidizing species are generated as needed, avoiding the need to store hazardous decontaminants.

25 Claims, 3 Drawing Sheets

ELECTROLYTIC SYNTHESIS OF PERACETIC ACID AND OTHER OXIDANTS

This application claims the benefit of the Feb. 6, 1998, filing date of Provisional Application Ser. No. 60/073,905.

BACKGROUND OF THE INVENTION

The present invention relates to the sterilization and disinfection arts. It finds particular application in conjunction with electrochemically produced solutions containing oxidizing agents, such as peracetic acid, hydrogen peroxide, and ozone, for sterilization or disinfection of medical and pharmaceutical equipment, and will be described with particular reference thereto. It should be appreciated, however, that the invention is also applicable to other sterilization, disinfection, and sanitization methods employing such oxidizing agents, including treatment of water, food, food service equipment, and the like.

Oxidizing agents, such as peracetic acid, hydrogen peroxide, and ozone, are useful disinfectants and sterilants for a variety of applications. Peracetic acid has a number of uses, including disinfection of waste and sterilization of medical equipment, packaging containers, food processing equipment, and the like. Peracetic acid poses few disposal problems because it decomposes to compounds which are readily degraded in sewage treatment plants. It has a broad spectrum of activity against microorganisms, and is effective even at low temperatures. Hydrogen peroxide is used for sterilization of medical equipment. Ozone has been used extensively for disinfection and treatment of water and, more recently, for treatment of food and food service equipment.

Conventionally, to form peracetic acid, peracetic acid precursors are mixed with water and other chemicals in a bath. Items to be decontaminated, either by sterilization or disinfection, are then immersed in the bath for a sufficient period to effect the required level of decontamination. The decontaminated items are then typically rinsed before use. To ensure effective sterilization or disinfection within a preselected period of time, the concentration of peracetic acid is maintained above a minimum effective level, typically around 2300 ppm for sterilization of medical instruments. When the peracetic acid concentration is at or above the minimum effective level for sterilization, complete sterilization is expected. Lower levels of peracetic acid are effective as disinfectants. Concentrations as low as 2–10 ppm, or less, have been shown to be effective for disinfection, which requires only the destruction of pathogenic microorganisms.

In facilities where items are being sterilized or disinfected at frequent intervals throughout the day, the same batch of peracetic acid solution is often used repeatedly. However, peracetic acid tends to decompose over time. For example, a bath which is above the minimum effective peracetic acid concentration for sterilization of around 2300 ppm at the beginning of a day, frequently drops to around 800 ppm, well below the effective concentration, without further additions of the peracetic acid precursors. Elevated ambient temperatures, the quantity of items sterilized or disinfected, and the degree of contamination of the items, all contribute to reducing the useful life of the bath. In addition, storage conditions sometimes lead to degradation of the peracetic acid precursors before use.

Moreover, the precursors are often hazardous materials which sometimes pose shipment and storage problems. Because of the risks of storage and also the fact that they degrade over time, it is preferable to maintain a limited supply of the precursors and reorder them at frequent intervals.

For hydrogen peroxide and ozone, similar problems arise. Ozone is a particularly short lived species which decomposes readily. Hydrogen peroxide tends to decompose to water and oxygen.

Recently, the cleaning and decontamination properties of solutions formed by the electrolysis of water under special conditions have been explored. Electrolysis devices are known which receive a supply of water, such as tap water, commonly doped with a salt, and perform electrolysis on the water. During electrolysis, an anolyte solution is produced from the doped water at an anode and a catholyte solution is produced at a cathode. Examples of such water electrolysis units are as described in U.S. Pat. Nos. 5,635,040; 5,628,888; 5,427,667; 5,334,383; 5,507,932; 5,560,816; and 5,622,848, whose disclosures are incorporated herein by reference.

To create these anolyte and catholyte solutions, tap water, often with an added electrically or ionically conducting agent such as halogen salts including the salts sodium chloride and potassium chloride, is passed through an electrolysis unit or module which has at least one anodic chamber and at least one cathodic chamber, generally separated from each other by a partially-permeable barrier. An anode contacts the water flowing in the anodic chamber, while a cathode contacts the water flowing in the cathodic chamber. The anode and cathode are connected to a source of electrical potential to expose the water to an electrical field. The barrier may allow the transfer of selected electron carrying species between the anode and the cathode but limits fluid movement between the anodic and cathodic chambers. The salt and minerals naturally present in and/or added to the water undergo oxidation in the anodic chamber and reduction in the cathodic chamber.

An anolyte resulting at the anode and a catholyte resulting at the cathode can be withdrawn from the electrolysis unit. The anolyte and catholyte may be used individually or as a combination. The anolyte has been found to have antimicrobial properties, including anti-viral properties. The catholyte has been found to have cleaning properties.

However, electrochemically activated water is not without shortcomings. Electrochemically activated water has a high surface energy which does not readily allow for penetration of the electrochemically activated water into creviced areas of medical instruments. Thus, complete kill may not be achieved. Further problems have arisen on metal surfaces coming into contact with the electrochemically activated water, including the surfaces of the decontamination equipment and metal medical devices. The electrochemically activated water is corrosive to certain metals. Stainless steel, used to produce many medical devices, is particularly susceptible to corrosion by electrochemically activated water.

Other chemicals are also amenable to electrochemical conversion. Khomutov, et al. ("Study of the Kinetics of Anodic Processes in Potassium Acetate," *Izv. Vvssh. Uchebn. Zaved., Khim. Teknol*. 31 (11) pp. 71–74 (1988)) discloses a study of the conversion of acetate solutions to peracetic acid and acetyl peroxide in the temperature range of −10° C. to 20° C. using a three-electrode cell. The anode and cathode regions of the cell were separated by a barrier of porous glass. Anodes of platinum, gold or carbon, at a potential of 2–3.2 V relative to a silver/silver chloride reference electrode, were used in the study. Potassium acetate concentrations were initially 2–10 mol/L. From conductivity and viscosity measurements, Khomutov, et al. estimated that peracetic acid solutions were generated at the anode with concentrations of active oxygen of 0.1 gram equivalents/L. However, no direct measurements of peracetic acid concentration in the bulk solution were made. Moreover, the pH range of 8.2–10.4 disclosed by Khomutov, et al. is undesirable for many practical decontamination solutions. To reduce corrosion of the metal components of the instruments to be decontaminated, a pH of close to neutral is desirable.

The present invention provides a new and improved system for generation of peracetic acid and other oxidizing agents which overcomes the above referenced problems and others.

SUMMARY OF THE INVENTION

According to one aspect of the invention, a method for preparing an antimicrobial solution containing an oxidizing species is provided. The method includes the steps of:

separating an anodic chamber and a cathodic chamber of an electrochemical cell with a barrier which is substantially impermeable to the oxidizing species; and applying a positive potential to an anode in the anodic chamber to convert a precursor in an electrolyte adjacent at least one of the anode and the cathode to the oxidizing species.

According to another aspect of the present invention, a composition for antimicrobial decontamination includes a plurality of oxidizing species generated by the method described above.

According to yet another aspect of the present invention, a method of antimicrobial decontamination is provided. The method includes the steps of separating an anodic chamber and a cathodic chamber of an electrochemical cell with a barrier which is substantially impermeable to an oxidizing species;

applying a positive potential to an anode in the anodic chamber to convert a precursor in an electrolyte adjacent at least one of the anode and the cathode to the oxidizing species;

transporting the oxidizing species to a site at which items are to be antimicrobially decontaminated; and, contacting the items with a solution containing the oxidizing species to antimicrobially decontaminate them.

According to a still further aspect of the present invention, a system for antimicrobial decontamination is provided. The system includes an electrochemical cell having an anode and a cathode separated by a barrier which is substantially impermeable to an oxidizing species. A source of an electrical potential is connected to at least one of the anode and the cathode. An electrolyte is adjacent at least one of the anode and the cathode, a precursor in the electrolyte being convertible to an oxidizing species by the application of a potential to at least one of the anode and the cathode. A fluid flow path transports electrolyte containing the oxidizing species from the electrochemical cell to a site at which items are to be decontaminated.

One advantage of the present invention is that it enables peracetic acid solutions to be prepared in situ, as required.

Another advantage of the present invention is that storage and shipment of hazardous sterilants is avoided.

Another advantage of the present invention is that it enables the concentration of peracetic acid in a microbial decontamination bath to be maintained during repeated use of the bath.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
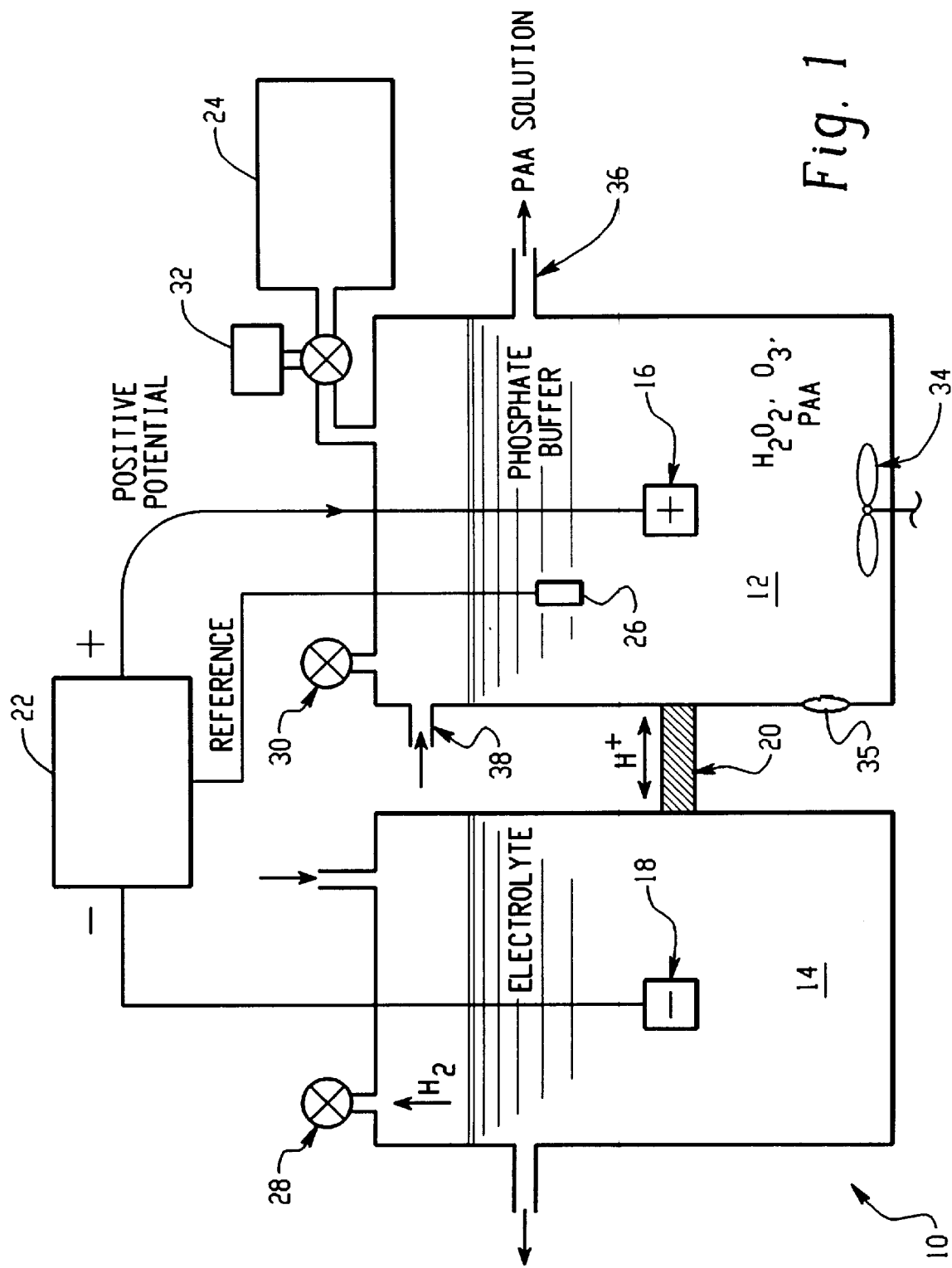
FIG. 1 is a schematic diagram of a preferred embodiment of an electrolysis unit for generation of sterilizing and disinfecting solutions of the present invention.
Figure 2:
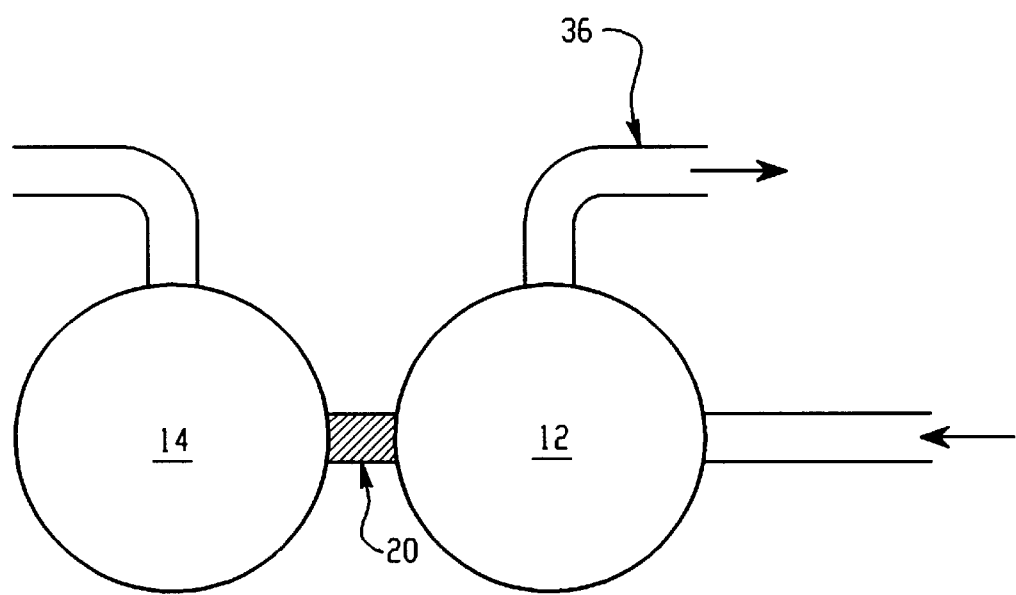
FIG. 2 is a top view of an electrolysis unit of the present invention; and, FIG. 3 is a plumbing diagram of a sterilization or disinfection system including the electrolysis unit of FIG. 1, a reagent cup receiving well and a reagent cup.

With reference to FIGS. 1 and 2, an electrochemical cell or electrolysis unit 10 generates oxidizing species for use as liquid sterilants and disinfectants, such as peracetic acid, hydrogen peroxide, and ozone. The unit 10 includes two electrode chambers, namely an anodic chamber 12 and a cathodic chamber 14. An electrode is disposed in each of the chambers. Specifically, an anode 16 is supported within the anodic chamber and a cathode 18 is supported within the cathodic chamber. A barrier or membrane 20 connects the anodic and cathodic chambers 12,14 and controls the flow of dissolved species between them. The barrier is preferably substantially impermeable to at least one of the oxidizing agents. A preferred barrier is an ion-specific membrane, such as a proton permeable membrane, which permits the migration of hydrogen ions between the chambers but limits mixing of other species within the two chambers. One such proton permeable membrane, NAFION™117, is available from DuPont and Aldrich. Alternatively, filter paper, such as Fisher brand P-5 filter paper, is used for the barrier 20.

A source of electric potential 22 applies a positive potential to the anode. The positive potential is selected to be high enough for the generation of oxidizing species at the anode, without simply causing the dissociation of water to oxygen and hydrogen at the electrodes. A potential of around +1.6 to +5 volts, relative to Ag/AgCl in 3 M NaCl, is preferred for this purpose, with a particularly preferred potential of around 3.2 V.

For generating the oxidizing species, at least the anodic chamber 12 receives an electrolyte solution. The electrolyte solution includes a precursor which is oxidized to the oxidizing species in the anodic chamber. Solutions formed from the electrolyte solution in the anodic and cathodic chambers during electrolysis are referred to as the anolyte and catholyte, respectively. In the case of peracetic acid generation, for example, the anolyte comprises a solution of peracetic acid. Other oxidizing species may also be present.

Optionally, a precursor reservoir or holding tank 24 is provided in fluid communication with the anodic chamber to hold a solution of the precursor. The precursor solution is delivered to the anodic chamber from the holding tank by a pump, gravity feed, or other convenient means. Alternatively, a solid precursor is carried in solution to the anodic chamber, as will be described in detail later.

The anode 16 preferably has a large surface area and includes a material which facilitates formation of oxidizing species at the anode. Suitable materials include, but are not limited to, carbon (including graphite), platinum, iridium, lead dioxide, and ruthenium oxide. In the case of lead dioxide or ruthenium oxide, the oxide is preferably disposed on a substrate, such as a titanium wire mesh or other noble metal substrate, which supports the oxide and provides the anode with a large surface area for generation of oxidizing species. Shepelin, et al.(*Élektrokhimiya*, Vol. 26, No. 9., pp. 1142–1148 (1990)) and Chernik, et al. (*Élektrokhimiya*, Vol. 33, No. 3., pp. 289–292 (1997)) disclose lead dioxide electrodes for ozone electrosynthesis, and are incorporated herein by reference.

The cathode is formed from any suitable electron acceptor, such as platinum, titanium, gold or carbon (including graphite). Carbon, such as graphite, is particularly preferred for generation of hydrogen peroxide, while platinum is preferred for generation of peracetic acid. Optionally the anodic chamber is fluidly connected with a reference electrode 26, such as a silver/silver chloride, to ensure that the selected applied potential is being maintained.

Pressure relief valves 28 and 30 are optionally provided to relieve excess pressure buildup within the anodic and cathodic chambers.

In the generation of peracetic acid, for example, the oxidizing species generated in the anodic chamber may include a variety of both short lived and longer living species which react directly with the peracetic acid precursor to form peracetic acid or which participate in reaction paths which lead to the formation of peracetic acid from the precursor. Such additional species include ozone, a short lived, but highly oxidizing species, and hydrogen peroxide, a longer living species which is an important intermediate in conventional methods of peracetic acid synthesis.

Optionally, an amount of hydrogen peroxide is added to the electrolyte in the anodic chamber as an initiator to initiate the reaction or combination of reactions which result in the formation of peracetic acid. A peroxide chamber 32 in fluid communication with the anodic chamber supplies the chamber with such hydrogen peroxide. Other chemicals may also be added to the anodic chamber as initiators, such as perborate, which raises the concentration of hydrogen peroxide in the anolyte solution.

Preferred peracetic acid precursors include acetic acid and other acetyl donors, such as sodium acetate, potassium acetate, acetic acid, and acetaldehyde. A particularly preferred acetyl donor is potassium acetate. Sodium acetate is also an effective donor, but tends to be less soluble in the electrolyte. When acetic acid is used as the precursor, it is preferably added to the anodic chamber at such a rate as to allow the pH to be maintained within the selected range for generation of oxidizing species. Dropwise addition of the acetic acid at the same rate as it is consumed is a suitable means of addition.

The preferred concentration of the precursor in the electrolyte is dependent on the solubility of the precursor and on the desired concentration of the oxidizing species. For forming peracetic acid from potassium acetate for example, the concentration of potassium acetate in the electrolyte is preferably within the range of from around 0.5 M to around 5 M.

A buffering system is optionally added to the electrolyte in the anodic chamber to maintain the electrolyte at an appropriate pH for generating the desired oxidizing species. The particular oxidizing species or intermediates generated, and their respective concentrations are dependent, to some degree, on the pH selected. At around neutral pH, i.e. from about pH6 to about pH8, generation of ozone is favored. As the pH increases, generation of hydrogen peroxide increases. Thus, for hydrogen peroxide, an electrolyte with a slightly alkaline pH is preferred, preferably around 7–9, most preferably around pH 8 or slightly above.

For preparation of dilute solutions of oxidizing species suitable for use as sterilants and disinfectants, a pH of around neutral is preferred. Phosphates of alkali metals are suitable buffers. One preferred buffering system includes a combination of monosodium phosphate, disodium phosphate and tripolyphosphates. Such a buffering system also provides anticorrosion properties. Another preferred buffering system includes one or more potassium phosphates. Sodium hydroxide may be added to raise the pH. Other buffering systems or pH adjusters useful in the generation of ozone and peracetic acid include sulfuric acid and perchlorate.

The electrolyte used in the anodic and cathodic chambers is preferably the same, in terms of the buffers and other additives employed, although different electrolytes are also contemplated.

Preferably, the pressure within the cell is above atmospheric. By way of example, electrolysis under a pressure of 10 p.s.i.g. approximately doubles the rate of peracetic acid production from potassium acetate, as compared to electrolysis performed at atmospheric pressure, and greater increases are to be expected at even higher pressures.

Optionally, a stirrer 34, such as a magnetic or mechanical stirrer, stirs the anolyte. The temperature of the anolyte solution is preferably in the range of from the freezing point of the anolyte to about 60° C, depending on the composition of the anode and species to be generated. For peracetic acid generation, a temperature of from about 0° C. to about 60° C. is preferred.

To maintain the temperature within this range, the electrolysis unit is optionally refrigerated, such as by immersion in an ice bath, or other cooling device, or by circulating a portion of the anolyte and catholyte through a heat exchanger. Alternatively, the temperature is maintained by withdrawing a portion of the anolyte at intervals, or continuously, and replacing it with fresh precursor solution, or by recirculating the anolyte via a decontamination system, as will be discussed in greater detail below.

Alternatively, the electrolysis is carried out at temperatures of room temperature and above, avoiding the need for refrigeration altogether. Where heated decontaminant solutions are desired, the sterilants and disinfectants are optionally generated in a heated electrolysis unit.

Corrosion inhibiting and surface energy reducing additives are optionally introduced into the peracetic acid solution, either by adding them to the anolyte prior to electrolysis or during or subsequent thereto. Other additives, including, but not limited to, detergents, chelators and sequestering agents, may also be added to the solution, either in combination with the other additives, or separately.

The corrosion inhibitory agents are selected in accordance with the nature of the materials in the items being cleaned and/or decontaminated with the oxidizing species. Corrosion inhibitors which protect against corrosion of aluminum and steel, including stainless steel, include phosphates, sulfates, chromates, dichromates, borates, molybdates, vanadates, and tungstates. Some additional aluminum corrosion inhibitors include 8-hydroxyquinoline and ortho-phenylphenol.

More specifically, phosphates are preferred for inhibiting stainless steel corrosion. Preferred phosphates include, but are not limited to, monosodium phosphate (MSP), disodium phosphate (DSP), sodium tripolyphosphate (TSP), sodium hexametaphosphate (HMP), and sodium sulfate either alone or in combination. Preferred borates include sodium metaborate ($NaBO_2$) Copper and brass corrosion inhibitors include triazoles, azoles, benzoates, tolyltriazoles, dimercapto-thiadiazoles, and other five-membered ring compounds. Particularly preferred copper and brass corrosion inhibitors include sodium salts of benzotriazole and tolyltriazole which are preferred due to their stability in the presence of strong oxidizing compounds. Mercaptobenzothiazole can also be utilized but is apt to be oxidized or destabilized by strong oxidizers. Salicylic acid is an example of an acceptable benzoate corrosion inhibitor.

In hard water, phosphate buffers and corrosion inhibitors tend to cause calcium and magnesium salts present in the hard water to precipitate and coat the instruments being decontaminated and/or cleaned and also leaves deposits on parts of the electrolysis system. In such cases, a sequestering agent appropriate to prevent precipitation such as sodium hexametaphosphate (HMP), or trisodium nitrolotriacetic acid (NTA $Na_3$) is preferably provided. Because sodium hexametaphosphate is also a corrosion inhibitor, it serves a dual purpose, both as a corrosion inhibitor and as a sequestering agent. Other sequestering agents include sodium polyacrylates. Of course, if soft or deionized water is utilized, the sequestering agent may be eliminated. However, to ensure universal applicability with any water that might be utilized, the presence of a sequestering agent is preferred.

A surface energy reducing agent is optionally added to the peracetic acid solution to increase penetration into crevices of items being treated. This is particularly important when cleaning and decontaminating complex medical instruments which may contain microbial contaminants in crevices, joints, and lumens. Surface energy reducing agents usable in accordance with the present invention include various wetting agents. Such wetting agents include anionic, cationic, nonionic, amphoteric, and/or zwitterionic surfactants. Specific classes of wetting agents which are useful include anionic and nonionic surfactants or combinations thereof. Examples of nonionic wetting agents usable in the present invention include surfactants such as fatty alcohol polyglycol ethers, nonylphenoxypoly (ethyleneoxy) ethanol, and ethoxylated polyoxypropylene. Specific examples include Genapol UD-50™, Igepal™, Fluowet™, and Pegal™. The wetting agents set forth above may be used alone or in combination with each other.

Amounts of corrosion inhibitor and wetting agents to be added to the peracetic acid solution will vary depending upon the type of agent being added and whether or not one or more agents are added.

The inorganic corrosion inhibitors are preferably present in amounts ranging from about 0.01% to 20.0% weight per volume (w/v). organic corrosion inhibitors are preferably present in amounts ranging from about 0.01% to 5.0% w/v. Phosphates are effective at concentrations in the range of about 0.01% to about 11.0% w/v.

The wetting agents are preferably present in amounts ranging from about 0.0001% to about 5.0 w/v. More preferably, the wetting agent is present in amounts ranging from about 0.0001% to about 0.5% w/v.

In a closed system under pressure, a septum 35 optionally permits withdrawal of anolyte samples for chemical analysis for monitoring concentrations of oxidizing species, precursors, or other additives.

The electrolysis unit 10 thus described has a wide variety of uses. Dilute solutions of the oxidizing species generated, such as peracetic acid, are advantageously used for sterilization or disinfection, although the peracetic acid, or other oxidizing species generated, is optionally used for other purposes. In one preferred embodiment, the unit is used for generating batches of peracetic acid solution which can be used immediately, for disinfecting or sterilizing items, or stored for later use. The acetic acid or other precursor is added to the unit and a corresponding oxidizing potential is applied until a desired concentration of peracetic acid is reached. The applied potential is then turned off and the solution leaves the anodic chamber through an outlet line 36. At relatively low pressures, the unit readily produces peracetic acid concentrations suitable for disinfection purposes. Peracetic acid concentrations of 10–20 ppm, ozone concentrations of up to about 1.6 ppm, and hydrogen peroxide concentrations of up to about 10 ppm are readily obtained. At higher pressures, more concentrated peracetic acid solutions are optionally generated.

In another embodiment, shown in FIG. 2, the unit is used to produce a stream of peracetic acid solution, which is withdrawn from the anodic chamber as it is generated through outlet line 36 and carried directly to the items to be decontaminated. An inlet line 38 replenishes the anodic chamber with a solution which includes the peracetic acid precursor. The embodiment is suited to a variety of purposes, such as decontamination of equipment, including food processing and pharmaceutical equipment, for disinfecting packaging such as food containers, and for sterilizing waste and water.

A third embodiment includes the recirculation of a sterilant or disinfectant solution from a vessel containing items to be sterilized or disinfected, through the anodic chamber of the electrolysis unit, and back to the vessel. The solution is preferably recirculated in this way until the desired peracetic acid concentration is achieved. Once the desired concentration is achieved the recirculation may be continued intermittently to maintain the desired peracetic acid concentration. Alternatively, the solution is recirculated continuously and the positive potential applied intermittently to maintain the concentration.

Figure 3:
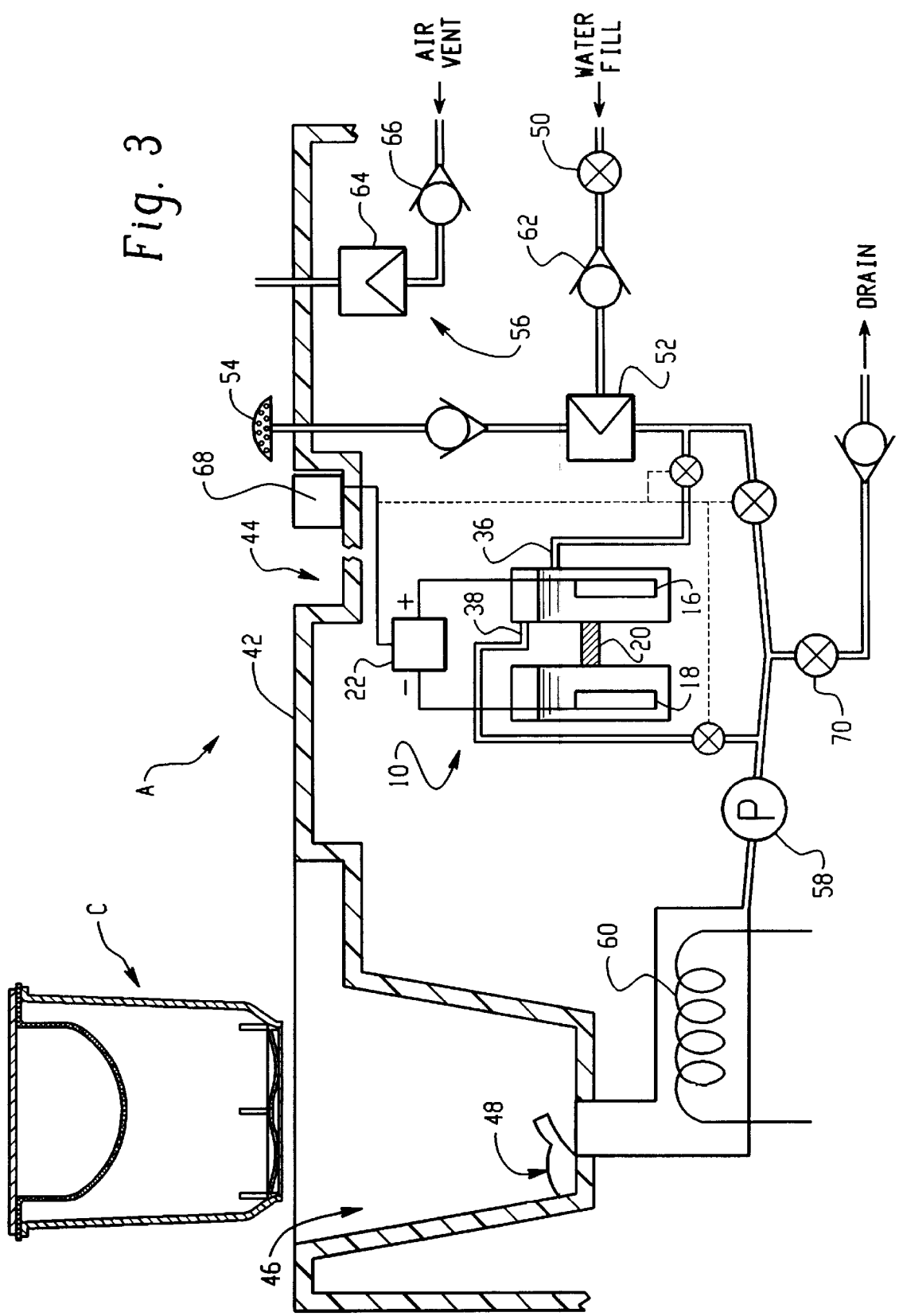

With reference to FIG. 3, a system for recirculating oxidizing species, such as peracetic acid, through a decontamination system includes the electrolysis unit 10 and a microbial decontamination apparatus A, which is configured to sit on a counter top or other convenient work surface. While the system is described herein with particular reference to peracetic acid, it should be appreciated that by varying the precursor composition, pH, electrode materials, and the like, as previously described, different oxidizing species, or combinations thereof, are alternatively employed.

A door or lid 40 is manually openable to provide access to a tray 42 which defines a receiving region 44 for receiving items to be microbially decontaminated. In the illustrated embodiment, the tray 42 is configured to receive devices, such as endoscopes or other long, coilable items. Other trays with item receiving regions of different configurations for receiving the items themselves or item holding containers are also contemplated. A well 46 preferably receives a unit dose of reagents for forming a sterilant, disinfectant, or other microbial decontaminating solution. The dose of reagents includes a peracetic acid precursor, preferably in a solid form, such as sodium or potassium acetate. Alternatively, the peracetic acid precursor, which may be liquid or solid, is added to the electrolysis unit from vessel 24, or by other suitable means.

A reagent containing package C, which contains the dose of reagents, is inserted into the well 46. Optionally, the peracetic acid precursor is contained separately from the other reagents within the cup. Once the items are loaded into the tray and the reagent carrying package C is inserted into the well, the lid 40 is closed and latched. A lower opener projection or member 48 is disposed at the bottom of the well 46 for engaging a lower surface of the package C as it is inserted into the well. The projection 48 cuts, or otherwise creates an opening in the cup, allowing the circulating water to dissolve or entrain the dose of reagents.

The water and reagents are circulated through the electrolysis unit until a selected concentration of peracetic acid is reached. Optionally, a fill valve 50 passes water through a microbe removing filter 52 in flow paths of a fluid circulating system. The microbe removing filter 52 blocks the passage of all particles of around 0.2μw or larger. The incoming water, which has passed through the filter, is directed through a spray or distribution nozzle 54 and fills the item receiving region 44 in the tray 42. As additional water is received, it flows into the well 46 dissolving solid reagents, or entraining liquid reagents, in the cup C, forming a solution. Filling is continued until all air is forced through an air system 56 and an entire interior volume is filled with the water. After the fill valve 50 is closed, a pump 58 circulates the fluid through the item receiving region 44 of the tray, the well 46, the electrolysis unit 10, and, optionally, a heater 60. The pump also forces the anti-microbial solution through the filter 52 to a check valve 62 decontaminating the filter. Further, the pump forces the anti-microbial solution through another microbe filter 64 in the air system 56 to a check valve 66. The circulation is continued until sterilization or disinfection is achieved.

A peracetic acid concentration sensor 68 optionally senses the concentration of peracetic acid in the decontamination apparatus A. In a preferred embodiment, the concentration sensor controls the application of the potential across the anode 16 and cathode 18. In an alternate embodiment, the concentration sensor controls the valves which direct flow, through and around the electrolysis unit 10 to control concentrations in the decontamination apparatus.

When decontamination is complete, a drain valve 70 is opened, allowing the solution to drain. Optionally, the drain valve is fluidly connected to the electrolysis unit for carrying the used peracetic acid solution back to the unit for destruction of oxidizing species. Air is drawn through the microbe filter 64 such that sterile air replaces the fluid within the system. Thereafter, the drain valve is closed and the fill valve 50 opened again to fill the system with a sterile rinse fluid.

While not intended to limit the invention, the following examples are illustrative of the methods of preparing the antimicrobial solutions containing one or more oxidizing agents.

EXAMPLE 1

Generation of Hydrogen Peroxide and Ozone in Sodium Hydroxide

The electrolysis unit of FIG. 1 was used to generate hydrogen peroxide and ozone. A pure graphite bar having a surface area of 21 cm$^2$ was used as the cathode. Prior to use, the cathode was anodized by the following procedure. The cathode was placed in 0.05 M $KH_2PO_4$ and the pH was adjusted to 6.88 with NaOH. A potential of +1.6 V was applied to the cathode versus an Ag/AgCl in 3 M NaCl reference electrode until a total charge of 0.566 C/cm$^2$ passed. A potential of −1.5 volts was then applied to the cathode for 1 minute.

The anodized cathode was then inserted into the electrolysis unit, together with a platinum anode. 0.1 M NaOH, at a pH of 12.54 was used as the precursor. A NAFION 117 proton exchange membrane 20 separated the cathodic and anodic chambers. Air was sparged through the catholyte for 30 minutes. A potential of +1.6 V versus the reference electrode was then applied to the platinum anode for 30 minutes, while air continued to be sparged. The potential was then raised to +2.5 V and held for a further 18.5 hrs. Hydrogen peroxide concentrations were measured using a CHEMetrics CHEMets analyzer. No hydrogen peroxide or ozone was detected at one hour. After 19.5 hrs, measurable amounts of these oxidizing agents were observed. (0.6 ppm $O_3$ in the catholyte, 2 ppm $H_2O_2$ in the anolyte.)

EXAMPLE 2

Generation of Peracetic Acid from Potassium Acetate at Alkaline pH The electrolysis unit of FIG. 1 was used in the generation of peracetic acid from a 5 M solution of potassium acetate at pH 9.15 . Two sheets of Fisher brand P-5 filter paper were used as the barrier. The anode and cathode were both platinum, with a surface area of 16.8 cm$^2$. An ice bath cooled the electrolysis unit to a temperature of around 8–12° C. The anode was maintained at a potential of +3.2 V. Peracetic acid concentration was measured spectrophotometrically over a 2 hour period in terms of absorbance. After 60 minutes the peracetic acid concentration rose from an initial absorbance of 0.008 abs to 0.010 abs. After 2 hours, the absorbance was 0.012 abs.

EXAMPLE 3

Generation of Peracetic Acid from Potassium Acetate at Near Neutral pH

The procedures used in Example 2 were repeated, except as noted. The anolyte and catholyte were prepared by adding sulfuric acid to 5 M potassium acetate, to bring the pH to 7.2. Potassium sulfate precipitate was removed and the solution introduced to the electrolysis unit. A potential of +3.2 V was applied to the anode versus the reference electrode. (Actual voltage applied 9.6 V.) Peracetic acid, hydrogen peroxide, and ozone measurements were made.

After 60 minutes, the peracetic acid concentration of the anolyte was 10.34 ppm and the hydrogen peroxide concentration was 3 ppm. An ozone concentration of 1.6 ppm was detected after 2 hours. The peracetic acid concentration reached 13.79 ppm after 90 minutes, but dropped thereafter, suggesting migration of oxidizing agents to the catholyte.

EXAMPLE 4

Generation of Peracetic Acid from Potassium Acetate at Near Neutral pH in the Presence of Potassium Fluoride and Monosodium Phosphate The procedure of Example 3 was followed, except as noted. The electrolyte was prepared using a 5 M potassium acetate, 0.2 g/L potassium fluoride, and 0.5 M monosodium phosphate solution. Sulfuric acid was added to bring the pH to 7.14 .

Peracetic acid and ozone measurements were made. After 60 minutes, at a potential of +2.5 V versus the reference electrode (actual voltage applied 9.6 V), the peracetic acid concentration in the anolyte was 6.33 ppm (0.010 abs). After 90 minutes, the concentration was 10.13 ppm (0.011 abs.) An ozone concentration of greater than 1 ppm was detected after 2 hrs.

EXAMPLE 5

Generation of Peracetic Acid and Ozone at Above Atmospheric Pressure

The procedures of Example 3 were used, except as noted. The pressure of the anolyte was maintained at between 2 and 6 p.s.i.g., and a NAFION PEM filter was used for the barrier 20. The 5 M potassium acetate electrolyte was adjusted to pH 6.98 with sulfuric acid.

0.6 ppm ozone was detected after 180 minutes. Peracetic acid concentration was measured every thirty minutes for 180 minutes, and reached a peak of 19.23 ppm at 120 minutes, falling to 7.69 ppm after 150 minutes.

EXAMPLE 6

Generation of Peracetic Acid, Hydrogen Peroxide, and Ozone at Above Atmospheric Pressure from Sodium Acetate The procedures of Example 5 were used, except as noted. A 2.5 M solution of sodium acetate, adjusted to pH 6.66 with sulfuric acid, was used as the electrolyte (a 5 M solution could not be prepared due to solubility problems). A potential of +4.77 V was applied versus the reference electrode (actual voltage applied 9.5 V). The pressure of the electrolyte in the electrolysis unit was maintained at between 2 and 10 p.s.i.g. by introducing air through the septum with a syringe.

Peracetic acid and hydrogen peroxide concentrations were measured at thirty minute intervals for 2 hours. The anolyte reached a maximum peracetic acid concentration of 4.55 after 90 minutes. Anolyte hydrogen peroxide concentration reached, and remained steady at 10 ppm after 60 minutes. 1 ppm ozone was detected in the anolyte after 120 minutes.

EXAMPLE 7

Generation of Peracetic Acid, Hydrogen Peroxide, and Ozone at Above Room Temperature, in the Presence of Surfactants and Corrosion Inhibitors A commercial anti-corrosion and surfactant composition containing phosphates and corrosion inhibitors, commonly used in peracetic acid sterilization, was added to a 5M Potassium acetate and the pH adjusted to 6.96 using sulfuric acid. After decanting of precipitate, the solution was added to an electrolysis unit with a platinum anode and a platinum cathode, separated by a NAFION PEM cell membrane. The electrolysis unit was placed in a heated water bath, which maintained the temperature within the electrolysis unit between 30 and 40° C. A potential of +4.46 V was applied vs. an Ag/AgCl in 3 M NaCl reference electrode.

After 30 minutes the peracetic acid and hydrogen peroxide concentrations were 2.7 and 5 ppm, respectively. The hydrogen peroxide concentration increased slightly in the following 1½ hours, while the peracetic acid concentration remained steady. Less than 1 ppm ozone was detected after two hours.

EXAMPLE 8

Generation of Peracetic Acid, Hydrogen Peroxide, and Ozone at Low pH, in the Presence of Surfactants and Corrosion Inhibitors The procedures of Example 7 were repeated with the following exceptions. The electrolysis unit was cooled with an ice bath and the pH adjusted to 5.96 with sulfuric acid. An initial potential of +4.8 V was applied vs. an Ag/AgCl in 3 M NaCl reference electrode. (Actual voltage applied was 9.5 V) After 30 minutes, the peracetic acid concentration was 2 ppm, rising to 4 ppm after 2 hours. The hydrogen peroxide concentration rose from around 5 ppm at 30 minutes, to around 10 ppm after 2 hours. Less than 1 ppm of ozone was detected after 2 hours.

EXAMPLE 9

Generation of Peracetic Acid, Hydrogen Peroxide, and Ozone from 0.5 M Potassium acetate, in the Presence of Surfactants and Corrosion Inhibitors The procedures of Example 7 were followed, except as noted. A low concentration of electrolyte was used. 0.5 M potassium acetate rather than 5 M potassium acetate was employed. The electrolysis unit was cooled in an ice bath to maintain a temperature of 13.5 –15° C. The pH of the electrolyte solution was adjusted to 6.93 using sulfuric acid. An initial potential of +4.28 V was applied vs. an Ag/AgCl in 3 M NaCl reference electrode. (Actual potential applied was 9.5 V). The peracetic acid concentration remained steady at 1.84 ppm after 30 minutes. The hydrogen peroxide concentration was 5 ppm after 30 minutes and 10 ppm after 2 hours.

EXAMPLE 10

Generation of Peracetic Acid, Hydrogen Peroxide, and Ozone in a Flow Cell

Generation of oxidizing species in a flow system was tested with a platinum anode and platinum cathode. in the electrolysis unit. 5M potassium acetate was used as the electrolyte with a NAFION PEM filter. The pH was adjusted to 6.71 with sulfuric acid and the anolyte and catholyte were circulated through separate flow paths and returned to the electrolysis unit. Two peristaltic pumps were used to recirculate the electrolyte solutions. Glass heat exchanger in a cooling bath cooled the solutions in the flow paths. The unit was run for 150 minutes.

The peracetic acid concentration remained steady at 1.71 ppm after 30 minutes. The hydrogen peroxide concentration reached 1 ppm after 1 hour and remained steady at 2 ppm after 1½ hours. 0.6 ppm of ozone was detected at 3 hours.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A method for preparing an antimicrobial solution containing an oxidizing species which includes peracetic acid and microbially decontaminating items therewith comprising:

separating an anodic chamber and a cathodic chamber of an electrochemical cell with a barrier which is substantially impermeable to the oxidizing species;

applying a positive potential to an anode in the anodic chamber to convert a precursor in an electrolyte adjacent at least one of the anode and the cathode to the oxidizing species;

adding a corrosion inhibitor to the electrolyte; and contacting the items with a solution containing the peracetic acid to microbially decontaminate them.

2. The method of claim 1, wherein the oxidizing species further includes another oxidizing species selected from the group consisting of ozone, hydrogen peroxide, and combinations thereof.

3. The method of claim 2, wherein the precursor includes an acetyl donor and wherein the oxidizing species includes peracetic acid.

4. The method of claim 3, wherein the acetyl donor is selected from the group consisting of potassium acetate, sodium acetate, acetic acid, acetaldehyde, and combinations thereof.

5. The method of claim 4, wherein the acetyl donor is potassium acetate, at a concentration of from about 0.5 to about 5 M.

6. A method of generating a peracetic acid antimicrobial solution comprising:

adding an acetyl donor to water to form an electrolyte with at least an 0.5 molar concentration of the acetyl donor;

receiving the electrolyte in an electrolytic cell having an anode and a cathode;

pressurizing the electrolytic cell to a pressure above atmospheric; and applying a positive potential to the anode and a negative potential to the cathode to generate a peracetic acid antimicrobial solution in which the concentration of the peracetic acid in the electrolyte is about 10 ppm or higher.

7. The method of claim 3, wherein the oxidizing species also includes ozone and wherein the concentration of the ozone in the electrolyte is up to about 1.6 ppm.

8. The method of claim 3, wherein the oxidizing species also includes hydrogen peroxide and wherein the concentration of the hydrogen peroxide in the electrolyte is up to about 10 ppm.

9. The method of claim 2, wherein the precursor includes sodium hydroxide and wherein the oxidizing species includes ozone and hydrogen peroxide.

10. The method of claim 1, wherein the electrolyte is buffered to a pH of around neutral or below.

11. The method of claim 1 wherein the electrolyte includes a buffer or pH adjuster selected from the group consisting of phosphates of alkali metals, such as monosodium phosphate, disodium phosphate, potassium phosphates, and tripolyphosphates; sodium hydroxide; sulfuric acid; perchlorate; and combinations thereof.

12. The method of claim 1, wherein the electrolyte further includes an additive selected from the group consisting of surfactants, sequestering agents, and combinations thereof.

13. The method of claim 1, wherein the electrolyte is subjected to a pressure of above atmospheric pressure.

14. A method for preparing an antimicrobial solution containing an oxidizing species comprising:

separating an anodic chamber and a cathodic chamber of an electrochemical cell with a barrier which is substantially impermeable to the oxidizing species;

applying a pressure of from about 2 to 10 p.s.i.g.;

applying a positive potential to an anode in the anodic chamber to convert a precursor in an electrolyte adjacent at least one of the anode and the cathode to the oxidizing species.

15. The method of claim 1, wherein the electrolyte is maintained at a temperature of between freezing and 60° C.

16. The method of claim 15, wherein the temperature is around room temperature or above.

17. The method of claim 1, wherein the precursor is added to the electrolyte incrementally.

18. A composition for antimicrobial decontamination comprising:

a plurality of oxidizing species generated by the method of claim 1.

19. The composition of claim 18, further including an additive from the group consisting of buffers, surfactants, corrosion inhibitors, sequestering agents, and combinations thereof.

20. A method of antimicrobial decontamination comprising:

separating an anodic chamber and a cathodic chamber of an electrochemical cell with a barrier which is substantially impermeable to an oxidizing species which includes peracetic acid;

applying a positive potential to an anode in the anodic chamber to convert a precursor in an electrolyte adjacent at least one of the anode and the cathode to the oxidizing species;

adding a corrosion inhibitor to the electrolyte;

transporting a portion of the electrolyte containing the peracetic acid and corrosion inhibitor to a site at which items are to be peracetic acid to microbially decontaminate them.

21. The method of claim 20, further including:

replenishing the precursor in the electrolyte.

22. The method of claim 20, further including recirculating the electrolyte and spent oxidizing species from the site to the electrochemical cell.

23. The method of claim 20, further including monitoring the concentration of the oxidizing species, and adjusting the rate at which the oxidizing species is generated.

24. A system for antimicrobial decontamination comprising:

an electrochemical cell including:

an anode and a cathode separated by a barrier which is substantially impermeable to an oxidizing species;

a source of an electrical potential connected to at least one of the anode and the cathode;

an electrolyte adjacent at least one of the anode and the cathode, a precursor in the electrolyte being convertible to an oxidizing species by the application of a potential to at least one of the anode and the cathode;

a container for receiving items to be decontaminated; and a fluid flow path for transporting the oxidizing species from the electrochemical cell to the container, in which the items are to be decontaminated, the electrochemical cell producing the oxidizing species on demand. as required for microbial decontamination.

25. The method of claim 10, wherein the electrolyte is buffered to a pH of 6 to 8 .

* * * * *